United States Patent [19]
Berg et al.

[11] Patent Number: 5,236,559
[45] Date of Patent: * Aug. 17, 1993

[54] SEPARATION OF HEXANE FROM VINYL ACETATE AND METHYL ACRYLATE BY EXTRACTIVE DISTILLATION

[75] Inventors: Lloyd Berg, 1314 S. Third Ave., Bozeman, Mont. 59715; Randi W. Wytcherley, Belgrade, Mont.

[73] Assignee: Lloyd Berg, Bozeman, Mont.

[*] Notice: The portion of the term of this patent subsequent to Jul. 6, 2010 has been disclaimed.

[21] Appl. No.: 8,356

[22] Filed: Jan. 22, 1993

[51] Int. Cl.⁵ .............................................. B01D 3/40
[52] U.S. Cl. ...................................... 203/57; 203/58; 203/63; 203/64; 203/65; 203/DIG. 10; 203/DIG. 21; 560/218; 560/248; 585/860; 585/862; 585/864; 585/865; 585/866
[58] Field of Search .................. 203/57, 63, 65, 64, 203/68, DIG. 10, DIG. 21; 560/248, 218; 585/860, 862

[56] References Cited

U.S. PATENT DOCUMENTS

| | | | |
|---|---|---|---|
| 2,171,795 | 9/1939 | Kautter | 203/65 |
| 3,394,057 | 7/1968 | Miller et al. | 203/DIG. 10 |
| 3,691,021 | 9/1972 | Feldman et al. | 203/65 |
| 3,736,236 | 5/1973 | Di Fiore et al. | 203/DIG. 10 |
| 4,464,229 | 8/1984 | Sato et al. | 560/218 |
| 4,897,161 | 1/1990 | Berg et al. | 203/51 |
| 4,925,533 | 5/1990 | Berg | 203/51 |
| 5,028,735 | 7/1991 | Segawa et al. | 203/70 |
| 5,106,460 | 4/1992 | Berg | 203/60 |

FOREIGN PATENT DOCUMENTS

| | | | |
|---|---|---|---|
| 45-36887 | 11/1970 | Japan | 560/218 |
| 47-37929 | 9/1972 | Japan | 560/218 |

Primary Examiner—Wilbur Bascomb, Jr.

[57] ABSTRACT

Hexane cannot be removed from hexane—vinyl acetate—methyl acrylate mixtures because of the ternary azeotrope. Hexane can be readily removed from hexane—vinyl acetate—methyl acrylate mixtures by extractive distillation. Typical effective agents are phenol, diethylene glycol methyl ether and 2-nitropropane.

1 Claim, No Drawings

SEPARATION OF HEXANE FROM VINYL ACETATE AND METHYL ACRYLATE BY EXTRACTIVE DISTILLATION

FIELD OF THE INVENTION

This invention relates to a method for separating hexane from vinyl acetate and methyl acrylate using certain higher boiling liquids as the agent in extractive distillation.

DESCRIPTION OF PRIOR ART

Extractive distillation is the method of separating close compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates. to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Extractive distillation would be an attractive method of effecting the separation of hexane from vinyl acetate and methyl acrylate if agents can be found that (1) will create a large apparent relative volatility between hexane, vinyl acetate and methyl acrylate and (2) are easy to recover from the vinyl acetate and methyl acrylate, that is, form no azeotrope with vinyl acetate or methyl acrylate and boil sufficiently above vinyl acetate and methyl acrylate to make separation by rectification possible with only a few theoretical plates.

Extractive instillation typically requires the addition of an equal amount to twice as much extractive agent as the three liquids on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Celcius degrees or more difference. It is also desirable that the extractive agent be miscible with overhead products otherwise it will form a two phase azeotrope with them and some other method of separation will have to be employed. Hexane, B.P.=68.7° C., vinyl acetate, B.P.=72.7° C. and methyl acrylate, B.P.=80.3° C. form a ternary azeotrope boiling at 65° C. and containing 68% hexane, 22% vinyl acetate and 10% methyl acrylate. Their relative volatility is 1.0 and separation by conventional rectification is impossible. Table 1 shows the number of plates required if agents can be found that will increase the relative volatility. A relative volatility of 3.0 will require only 17 plates to obtain 99.5% purity.

TABLE 1

Theoretical and Actual Plates Required vs. Relative Volatility

| Relative Volatility | Theoretical Plates Required At Total Reflux, 99.5% Purity | Actual Plates Required, 75% Efficiency |
|---|---|---|
| 1.2 | 76 | 100 |
| 1.35 | 46 | 61 |
| 1.50 | 34 | 45 |
| 2.0 | 20 | 27 |
| 2.5 | 15 | 20 |
| 3.0 | 12.5 | 17 |

OBJECTIVE OF THE INVENTION

The object of this invention is to provide a process or method of extractive distillation that will enhance the relative volatility between hexane, vinyl acetate and methyl acrylate in their separation in a rectification column. It is a further object of this invention to identify organic compounds which in addition to the above constraint are stable, can be separated from the vinyl acetate and the methyl acrylate by rectification with relatively few theoretical plates and can be recycled to the extractive distillation column and reused with little decomposition.

SUMMARY OF THE INVENTION

The objects of this invention are provided by a process for separating hexane from vinyl acetate and methyl acrylate which entails the use of certain organic compounds as the agent in extractive distillation.

DETAILED DESCRIPTION OF THE INVENTION

TABLE 2

Effective Extractive Distillation Agents

| Compounds | Relative Volatility | | |
|---|---|---|---|
| | Hex/VinAc | Hex/MeAcr | VinAc/MeAcr |
| Phenol | 3.0 | 6.1 | 2.1 |
| o-Cresol | 2.8 | 5.2 | 1.8 |
| m-Cresol | 2.9 | 5.9 | 2.0 |
| p-Cresol | 2.3 | 4.0 | 1.7 |
| 2-tert. Butyl phenol | 1.9 | 3.7 | 1.9 |
| 4-Ethyl phenol | 1.5 | 2.0 | 1.3 |
| 2,6-Dimethyl phenol | 1.7 | 2.9 | 1.7 |
| 2-Nitropropane | 1.7 | 2.4 | 1.3 |
| Benzyl alcohol | 1.5 | 2.4 | 1.6 |
| Diethylene glycol methyl ether | 2.2 | 3.2 | 1.4 |
| 1-Methyl-2-pyrrolidinone | 3.7 | 4.4 | 1.2 |
| 2-Methoxyethanol | 1.7 | 2.4 | 1.4 |

We have discovered that certain organic compounds will greatly improve the relative volatility of hexane to vinyl acetate and of vinyl acetate to methyl acrylate. The effective agents are listed in Table 2. Presented are the relative volatilities of hexane vs. vinyl acetate and vinyl acetate vs. methyl acrylate. The data in Table 2 was obtained in a vapor-liquid equilibrium still. The compounds which are effective are phenol, o-cresol, m-cresol, p-cresol, 2-tert. butyl phenol, 4-ethyl phenol, 2,6-dimethyl phenol, 2-nitropropane, benzyl alcohol, diethylene glycol methyl ether, 1-methyl-2-pyrrolidinone and 2-methoxyethanol.

WORKING EXAMPLES

Example 1

One hundred grams of the hexane—vinyl acetate—methyl acrylate azeotrope and 50 grams of phenol were charged to an Othmer type vapor-liquid equilibrium still and refluxed for five hours. Analysis of the vapor and liquid by gas chromatography gave a vapor composition of 87.5% hexane, 10.3% vinyl acetate and 2.2% methyl acrylate and a liquid composition of 66.6% hexane, 23.2% vinyl acetate and 10.2% methyl acrylate. This indicates a relative volatility of hexane to vinyl acetate of 3.0, hexane to methyl acrylate of 6.1 and vinyl acetate to methylacrylate of 2.1

Example 2

One hundred grams of the hexane—vinyl acetate—methyl acry azeotrope and 50 grams of diethylene glycol methyl ether were charged to the vapor-liquid equilibrium still and refluxed for five hours. Analysis gave a vapor composition of 78.3% hexane, 16.3% vinyl acetate and 5.4% methyl acrylate and a liquid composition of 59.7% hexane, 27.5% vinyl acetate and 12.8% methyl acrylate. This indicates a relative volatility of hexane to vinyl acetate of 2.2, of hexane to methyl acrylate of 3.2 and of vinyl acetate to methyl acrylate of 1.4.

We claim:

1. A method for recovering hexane from a mixture of hexane, vinyl acetate and methyl acrylate which comprises distilling a mixture of hexane, vinyl acetate and methyl acrylate in a rectification column in the presence of about one part of an extractive agent per part of hexane—vinyl acetate—methyl acrylate mixture, recovering the hexane as overhead product and obtaining the vinyl acetate, the methyl acrylate and the extractive agent from the stillpot, wherein said extractive agent consists of one material selected from the group consisting of phenol, o-cresol, m-cresol, p-cresol, 2-tert. butyl phenol, 4-ethyl phenol, 2,6-dimethyl phenol, 2-nitropropane, benzyl alcohol, diethylene glycol methyl ether, 1-methyl-2-pyrrolidinone and 2-methoxyethanol.

* * * * *